United States Patent [19]

Vas et al.

[11] E Re. 31,097

[45] Reissued Dec. 7, 1982

[54] APPARATUS AND METHOD FOR DETECTON OF BODY TISSUE MOVEMENT

[75] Inventors: Ran Vas, Encino; James S. Forrester, Malibu; George A. Diamond, Los Angeles, all of Calif.

[73] Assignee: Cardiokinetics, Inc., Seattle, Wash.

[21] Appl. No.: 160,384

[22] Filed: Jun. 17, 1980

Related U.S. Patent Documents

Reissue of:

[64] Patent No.: 4,182,315
Issued: Jan. 8, 1980
Appl. No.: 817,708
Filed: Jul. 21, 1977

[51] Int. Cl.[3] ..... A61B 5/02
[52] U.S. Cl. ..... 128/687; 128/700
[58] Field of Search ..... 128/687, 698, 695, 706, 128/710, 715, 722, 782

[56] References Cited

U.S. PATENT DOCUMENTS

| | | | |
|---|---|---|---|
| 2,241,190 | 5/1941 | Fenning | 128/722 |
| 3,773,033 | 11/1973 | Rodbard | 128/687 |
| 3,811,428 | 5/1974 | Van Horn et al. | 128/698 |
| 3,926,177 | 12/1975 | Hardway, Jr. et al. | 128/722 |
| 3,993,044 | 11/1976 | McGuffin | 128/782 |
| 4,066,069 | 1/1978 | Dolch | 128/706 |

FOREIGN PATENT DOCUMENTS 26039 6/1966 Israel .

OTHER PUBLICATIONS

Groom et al., "American Journal of Medical Electronics", Oct.-Dec. 1964, pp. 261-265.
Vas et al., "I.E.E.E. Transactions on Biomedical Engineering", V. 23, No. 1, Jan. 1976, pp. 49-54.

*Primary Examiner*—William E. Kamm
*Attorney, Agent, or Firm*—Robert J. Schaap

[57] ABSTRACT

An apparatus and method for the detection of movement of body tissues and, more particularly, movements of segments of the heart muscle and method for a noninvasive technique for the detection of coronary and arterial abnormalities. The apparatus includes a probe, preferably in the form of a detector plate, utilizing electric field measurement for detection of movements of a nearby segment of the body tissue, as for example, a segment of the heart muscle. The detector plate is coupled to a variable-frequency oscillator and phase-lock system for measuring capacitive change used to shift the phase of the oscillator when the detector is placed with respect to a certain body tissue. The apparatus employs its own unique system of timing heart movement in that the detector is capable of sensing a signal having a low frequency component which provides information regarding tissue movement. The detector also senses a high frequency component of the signal which represents closure of heart valves and thereby establishes a timing cycle for heart movement so that contraction and relaxation movements of the heart tissue can be measured in terms of the timing cycle of the heart. A filter in the apparatus separates the high frequency components from the low frequency components so that information regarding relaxation and contraction may be recorded simultaneously with the timing cycle of the heart movement.

82 Claims, 12 Drawing Figures

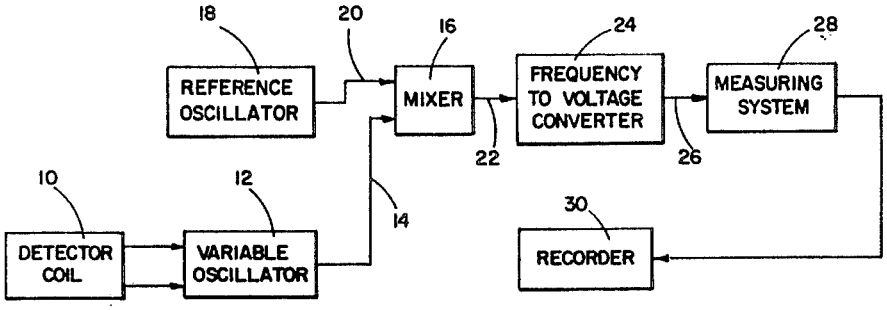
FIG. I (PRIOR ART)
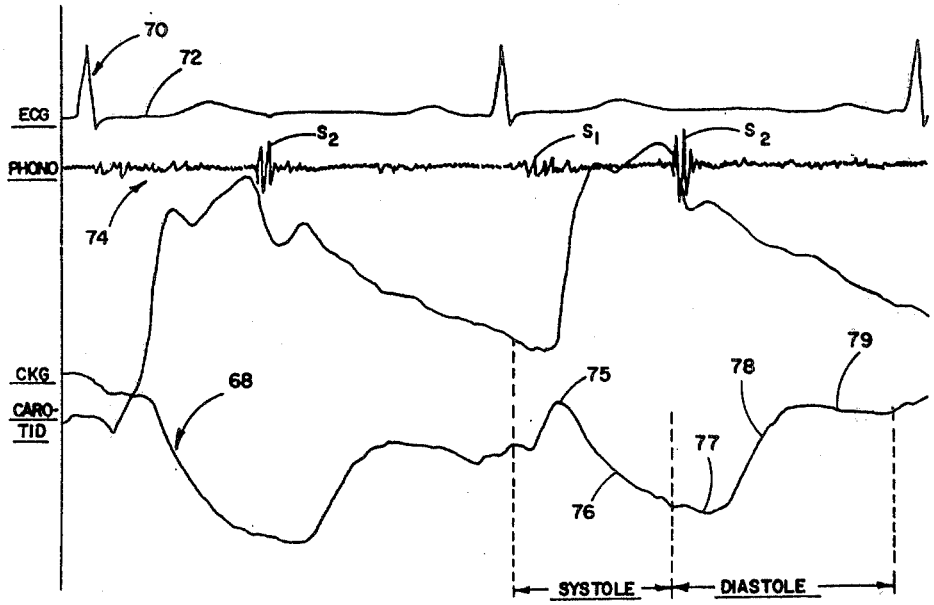
NORMAL CARDIOKYMOGRAM
FIG. II

APPARATUS AND METHOD FOR DETECTON OF BODY TISSUE MOVEMENT

Matter enclosed in heavy brackets [ ] appears in the original patent but forms no part of this reissue specification; matter printed in italics indicates the additions made by reissue.

BACKGROUND OF THE INVENTION

1. Purpose of the Invention

This invention relates in general to certain new and useful improvements in the measurement of body tissue movement by non-invasive techniques and, more particularly, to the detection of cardiovascular abnormality and apparatus and method for monitoring the condition of the human cardiovascular system.

2. Brief Description of the Prior Art

As is well known, coronary artery disease is the leading cause of death in the United States. About half of those affected are in apparent good health and are totally unaware that they have the disease. Accordingly, doctors and researchers in this area are still striving for a simple and safe method for early detection of the disease.

The only technique widely used in screening patients for coronary artery disease is electrocardiography, which provides a graphic tracing of the bioelectric potential of the heart muscle. When electrocardiography is used for coronary screening, an individual's electrocardiogram (ECG) is recorded first while the individual is at rest, and then after strenuous exercise, on the theory that the exercise produces a transient imbalance between the heart's oxygen supply, derived from the coronary artery blood flow, and its oxygen requirements, imposed by the work of exercise. Such an imbalance may be detected by the development of specific electrocardiographic abnormalities typical of coronary artery disease. Unfortunately, however, the electrocardiogram is relatively insensitive to this oxygen imbalance, and the probability of a successful diagnosis using electrocardiography is only about sixty percent in patients with symptoms suggestive of coronary artery disease. For those individuals exhibiting no apparent symptoms of the disease, the probability of correctly diagnosing its presence by electrocardiography alone is far lower. About half of those individuals who exhibit abnormal ECG's during a stress test, but are otherwise apparently healthy, do not actually have coronary artery disease.

There have been some attempts to use apex cardiograph determination which is based on a measurement of the relative movement of small segments of the chest wall over the cardiac apex. However, this measurement is a surface phenomena, is restricted to a small area, and is also relatively impractical in that it does not represent the true motion of the heart.

At present, then, there is no acceptable method for diagnosing or evaluating the severity of coronary artery disease short of cardiac catheterization, which involves direct injection of a chemical into both the coronary arteries and the heart chambers themselves. Although this is a highly reliable diagnostic tool, it is also relatively expensive and time consuming. Moreover, it involves significant risks to the patient, and is obviously unsuited for screening purposes.

In recent years, a number of animal laboratory investigations have shown that reduction in blood supply to the heart muscle, as occurs in human coronary artery disease, can be detected by studying the movements of segments of the heart. When a segment of the heart receives less oxygen than is normally required for proper function, as occurs with a partial obstruction of a coronary artery by atherosclerosis, the normal contraction pattern of cardiac muscle changes in a characteristic fashion. In simple terms, while the normal muscle segments of the heart continue to contract inward, the afflicted segment bulges outward. Then, as normal muscle segments relax and lengthen, the previously stretched, abnormal muscle segment shortens. Thus, the abnormal segment exhibits a movement similar in contour, but opposite in direction, to that of the normal segments.

Prior to this invention no one had succeeded in developing a noninvasive technique for diagnosing coronary artery disease in humans by identifying an abnormality, of the kind just described, in the movement of heart muscle segments. It is apparent that such a technique would include the principal steps of recording movements of a selected segment of the heart, precisely timing and identifying the direction of this movement in relation to the expected, normal pattern of movement during the entire cardiac cycle of contraction and relaxation, and transiently provoking a contraction abnormality of a muscle segment by some type of stress which induces an oxygen imbalance as described previously. The closest previous approximation to this approach can probably be found in those devices which recorded movement of the chest wall induced by total cardiac movement, such as the instruments known as the vibrocardiograph, the kinetocardiograph, and the apexcardiograph. These devices have been used during exercise, but have been found to be of no value in diagnosing coronary heart disease in man, and are no longer used in this manner.

It has been recognized for some time that an instrument known as a displacement cardiograph (DCG) could be used to detect physical movement of body tissue, including muscle segments of the heart. Such an instrument was described in a German "Offenlegungsschrift", No. 1,566,044, published on Apr. 2, 1970, and a corresponding Israeli Pat. No. 26,039, dated June 29, 1966. This latter device has also been described in various other publications, for example, "Electronic Device for Physiological Kinintic Measurements and Detection of Extraneous Bodies" by Ran Vas, published in IEEE Transactions on Biomedical Engineering, Vol. BME-14, No. 1, Jan., 1967, pages 2–6, and "The Displacement Cardiograph" by R. Vas et al, published in IEEE Transactions on Biomedical Engineering, Vol. BME-23, No. 1, Jan., 1976, pages 49–54.

The last mentioned publication also describes in general outline how a displacement cardiograph might be used as an apex cardiograph in the detection of ischemia. Significantly, however, the DCG has not been utilized in the detection and diagnosis of coronary artery disease. It is also noteworthy that use of the DCG for any study of heart movements requires an accompanying recording from a conventional instrument, such as an electrocardiograph and phonocardiograph in order to relate the DCG tracing to the timing of the cardiac cycle.

The basic apparatus of the DCG includes a constant or reference oscillator circuit; a variable oscillator circuit; an inductive detector coil connected to the variable oscillator circuit so as to determine, in part, the frequency of the variable oscillator circuit; a mixer circuit connected to receive input signals from the reference and variable oscillator circuits, and to provide an output signal having a frequency equal to the difference in input frequencies; a frequency-to-voltage converter circuit; and a recording system. The detector coil, although satisfactory for some applications of the DCG, does not have the necessary sensitivity for the accurate detection of movements of heart muscle segments, and also introduces significant distortion into the signal. The other circuit components together form a frequency-modulation system for deriving a body tissue displacement signal, and such a system, although satisfactory for many applications, does not provide the high degree of sensitivity needed in the accurate monitoring of heart segment movements.

Considering the DCG apparatus more specifically, it has been observed that one of the primary disadvantages of this apparatus and the method used thereby is that the apparatus operates by measurement of an electromagnetic field at the body tissue and utilizes an inductive change. In the frequency modulation system employed by the DCG apparatus, one frequency was compared to another. However, with spontaneous changes in oscillator or cardiac frequency, the sensitivity of the detector system would be altered considerably.

The present invention is far more effective than the DCG apparatus in that place changes are measured, as opposed to frequency changes, and the phase changes are considerably larger, thereby providing a much more accurate measurement. In addition, the apparatus of the present invention is far superior to the DCG apparatus in that the signal-to-noise ratio is improved due to the stability of the oscillator forming part of the present invention, and the fact that less electronic components are used.

One of the other problems with the DCG apparatus is that it effectively, though undesirably, functioned as a metal detector. This created a serious disadvantage in that many patients have been provided with metal components, as for example, artificial heart valves, cardiac pacemarkers, pacing electrodes, titanium vascular staples, wire sutures to close the sternum, and the like. Accordingly, these metal components materially interfere with any measurement to be obtained with the DCG apparatus.

Accordingly, the DCG apparatus has not been found to be entirely suitable for use in the detection of coronary artery disease. There is, therefore, still a great need for an instrument which obviates the aforedescribed shortcomings of the DCG, and thereby provides a convenient and reliable noninvasive technique for screening individuals to determine whether or not they have coronary artery disease or other forms of atherosclerotic vascular disease. The present invention satisfies this need.

OBJECTS OF THE INVENTION

It is, therefore, a primary object of the present invention to provide an apparatus capable of detection of body tissue movement in a given time frame (such as the cardiac cycle) and which utilizes electric field sensing adjacent to the external areas of the body of a person being tested.

It is another object of the present invention to provide an apparatus used in the detection of coronary or periphery artery disease and abnormalities, and which externally generates a precise timing movement of segments of the heart in relation to the cardiac cycle.

It is also an object of the present invention to provide an apparatus of the type stated which measures a signal representative of a sound signal and which contains a high frequency component providing information on the timing of the cardiac cycle and a low frequency component containing information regarding movement of the heart segments in a timed cardiac cycle.

It is a further object of the present invention to provide an apparatus of the type stated which uses electric field measurement as opposed to electromagnetic field measurement and provides a capacitive change used in conjunction with a phase-lock loop in order to obtain phase change measurement and thereby provides a much more sensitive apparatus.

It is an additional object of the present invention is provide a method for determining accurate movement of body tissue segments in relation to a timing cycle with respect to the body tissue movement.

With the above and other objects in view, our invention resides in the novel features of form, arrangement, and combination of parts presently described and pointed out in the claims.

SUMMARY OF THE INVENTION

The present invention resides in a method utilizing an apparatus termed "cardiokymographic" apparatus in the detection and diagnosis of coronary artery disease, and in the capability of the cardiokymographic apparatus to provide precise timing of the detected movements of a segment of the heart in relation to the cardiac cycle, without reference to an accompanying electrocardiogram or any other conventional cardiographic recording, which is required in some form or another with all other methods for recording cardiac movements, including the DCG.

Basically, the method of the invention includes the steps of detecting and recording movements of a segment of the surface of the heart of a person at rest, using the cardiokymographic apparatus; detecting and recording movement of the same heart segment during or after a stress condition, such as strenuous exercise; and, simultaneously with the foregoing steps, and using the cardiokymographic apparatus alone, detecting and recording valve closure sounds indicative of the precise onset and termination of specific portions of the cardiac cycle, i.e., contraction and relaxation. The final steps of the method are analyzing the cardiokymographic recordings so produced in relation to the portions of the cardiac cycle, to determine the presence and degree of any contraction abnormality of the heart segment due to coronary atherosclerosis, and determining from this analysis whether or not the person has coronary artery disease.

In the practice of this method, the cardiokymograph recordings have to be analyzed in relation to the cardiac cycle, i.e., there has to be some way of obtaining a time reference on the cardiokymograph recordings, in relation to the respective cycle of contraction and relaxation. Although this may be roughly estimated by means of a conventional electrocardiogram recorded simultaneously with the cardiokymographic data, one very important aspect of the invention involves detecting the closing movement of various heart valves during the cardiac cycle using the cardiokymographic apparatus itself. More specifically, the detection of heart valve movement includes the steps of filtering cardiokymographic signals to exclude those derived from relatively slow movements of a heart segment or segments being examined, and amplifying the remaining high-frequency vibrations (in the audio-frequency range) caused by valvular closure. These vibrations are transmitted to the external surface of the heart through the fluid medium, the blood, within the cardiac chamber.

The novel apparatus of the invention includes a number of important improvements over the earlier DCG apparatus. First, the apparatus of the invention includes filter means for separating movements of the heart in the audio-frequency range, due to valve closures and other phenomena to be further described, from movements in a lower-frequency range, due to heart muscle contraction and relaxation. This is accomplished by selective filtration and amplification of the cardiokymographic signals, to isolate those components which lie substantially in the audio-frequency range.

In this manner, signals indicative of heart sounds may be recorded simultaneously with signals indicative of heart movements, both types of signals being derived from a single detector. As a secondary consequence of separating the high-frequency components of segment movement due to valve closure from the low-frequency components due to cardiac motion, the quality of the signal representing contraction may be also substantially improved in fidelity.

The frequency spectrum of the primary movement event of the heart, i.e., the contraction and relaxation of the muscles, falls in the range 0–15 hertz (cycles per second). Movements at frequencies above 30 hertz are much lower in amplitude, but are in the audible range, and are detectable manifestations of the audible cardiac events, i.e., the valve closure sounds. Accordingly, the filter means can be chosen to have a high-pass characteristic with a cutoff frequency at approximately 30 hertz. The audio-frequency signals passed by the filter means can then be amplified and recorded as the valve closure sounds or even heart murmers. For this purpose, it is desirable to selectively filter signals with various frequency components.

The signal which is generated by the detector is divided into a first signal component representing myocardial motion and a second signal component representing mycardial sounds. In this case, this sound is essentially a vibration with a frequency of about slightly greater than zero to about 1,000 hertz. In essence, the normal sound frequency in the audible range is about 20 to about 20,000 hertz. However, the apparatus of the present invention is capable of detecting the signals representative of sound even down to about slightly above 0 hertz, although below 20 hertz, the signals essentially represent vibrations proportional to motions of the heart. Thus, the device of the present invention actually detects the signal representing sound within a range of about 0.1 hertz to about 500 hertz and, in many cases, higher than 500 hertz.

In the present invention, the bandpass filter divides the generated signal into a first signal component of about 0 to 30 hertz, and a second signal component of about 30 to 500 hertz. Actually, the first signal component could contain frequencies within the range of 0 to 500 hertz. The lower frequency signal carries information representing movement of the heart segments and the high frequency sound signal carries information representing the closure of the heart valves in order to determine timing of the heart cycle but is of such low amplitude that little distortion of the movmement signal occurs.

Another basic improvement in the cardiokymographic apparatus of the invention relates to the replacement of the inductive detector coil of the DCG with a capacitive detector plate which utilizes an electric field rather than a magnetic field in the detection of heart movements. This use of a plate and electric field provides greater sensitivity at all frequencies and significantly reduces signal distortion. These properties, in turn, allow the detection of the high-frequency valve movements with much greater fidelity than with the DCG, and also result in a significant improvement in the fidelity of the low-frequency recording of heart wall motion.

Yet another fundamental improvement over the DCG apparatus is that the cardiokymograph of the invention utilizes a phaselock system, rather than a frequency-modulation system, to obtain a signal indicative of the displacement of body tissue with respect to the detector. The phase-lock system includes a voltage-controlled oscillator, a phase comparator and an amplifier, the phase comparator being connected to generate an error signal indicative of a phase difference between input signals from the voltage controlled oscillator and the variable-frequency oscillator circuit. The error signal is amplified, fed back to the voltage-controlled oscillator, and is also utilized to provide an output signal indicative of the detected phase difference, and hence of the tissue displacement. The phase-lock system, with its use of phase difference rather than frequency difference, is much more sensitive to body tissue movements than the frequency-modulation system of the DCG apparatus.

It will be apparent from the foregoing summary that the present invention represents a highly significant advance in techniques for the detection and diagnosis of coronary artery disease and other related diseases. In particular, it provides a method and apparatus for the noninvasive detection of coronary artery disease without the need for other conventional equipment to indicate the timing of the cardiac cycle, and it provides a displacement signal of previously unobtainable sensitivity and fidelity.

Other aspects and advantages of the present invention will become apparent from the following more detailed description, taken in conjunction with the accompanying drawings.

BRIEF DESCRIPTION OF THE DRAWINGS

Figure 12:
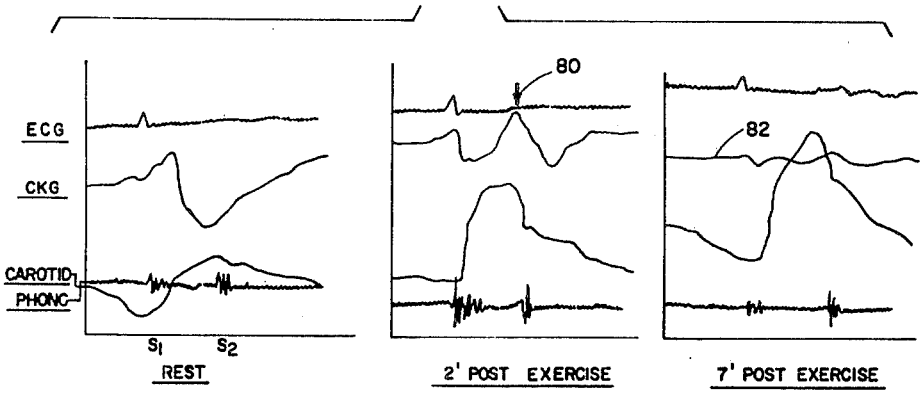
Figure 2:
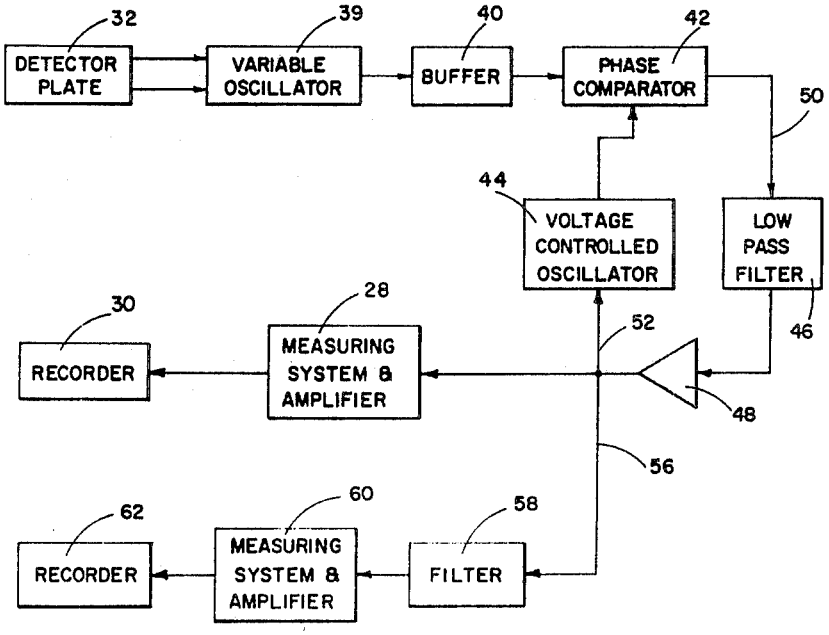
Figure 6:
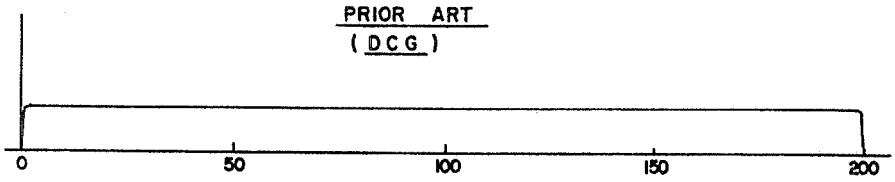
Figure 7:
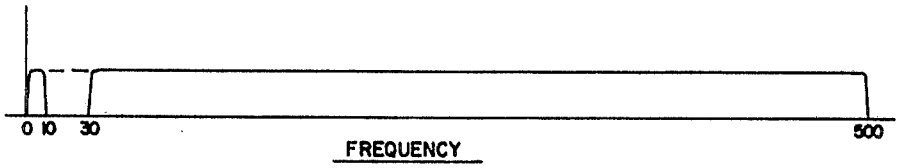
Figure 8:
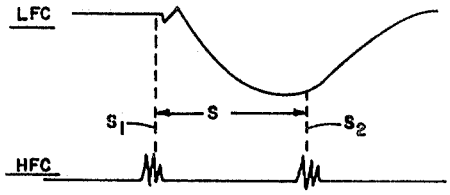
Figure 9:
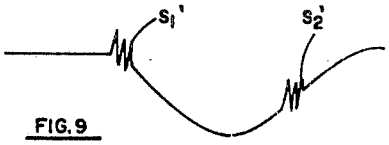
Figure 10:
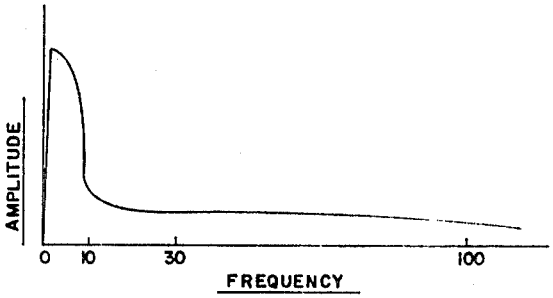
Figure 3:
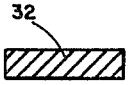
Figure 4:
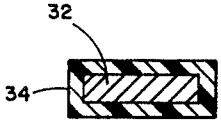
Figure 5:
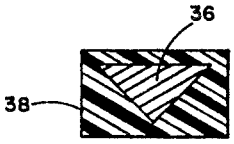

Having thus described the invention in general terms, reference will now be made to the accompanying drawings in which:

FIG. 1 is a schematic block diagram of a displacement cardiograph (DCG) apparatus of the prior art;

FIG. 2 is a schematic block diagram of a cardiokymographic apparatus of the present invention;

FIG. 3 is a vertical sectional view showing a form of detector plate which can be used with the apparatus of the present invention;

FIG. 4 is a vertical sectional view of another embodiment of a detector which can be used with the apparatus of the present invention;

FIG. 5 is a vertical sectional view of yet another embodiment of a detector which can be used with the apparatus of the present invention;

FIG. 6 is a schematic representation of a graph showing the frequency range of the signal in the displacement cardiograph apparatus of the prior art;

FIG. 7 is a schematic representation of a graph showing the frequency signal components obtained by the cardiokymographic apparatus of the present invention;

FIG. 8 is a schematic representation of a recorded high frequency component (HCF) and a recorded low frequency component (LFC) and showing the systolic phase of a cardiac cycle;

FIG. 9 is a schematic representation of a recorded high-frequency component and low-frequency component as combined;

FIG. 10 is a schematic representation of a graph showing the amplitude as a function of the frequency in the signal generated in accordance with the cardiokymographic apparatus of the present invention;

FIG. 11 is a reproduction of a cardiokymographic recording of the motion of a segment of the anterior wall of a normal human wall as taken with the apparatus of the present invention in conjunction with the simultaneously recorded conventional electrocardiogram, a phonocardiogram and a recording of the movement of the carotid artery, the cardiokymographic recording showning a normal inward movement during the period of cardiac contraction; and FIG. 12 is a set of three reproductions of cardiokymographic recordings similar to FIG. 11, but taken in a patient with coronary artery disease and showing, following stress, the development of an abnormal outward movement of a heart segment during the period of cardiac contraction.

DETAILED DESCRIPTION OF PREFERRED EMBODIMENTS

The present invention is concerned with improvements in an apparatus and method for measuring body tissue movement in a selected time frame established by the apparatus itself. Particularly, the invention is described in one embodiment in connection with the detection and diagnosis of coronary arterial disease and disorder, as for example, coronary arteriosclerosis. It should be understood, however, that the apparatus can be used in measuring other forms of body tissue movement in a selected time frame, as for example, peripheral arterial movement, eyeball movement and the like.

More specifically, the invention will be described with respect to an embodiment of a method for detecting and diagnosing coronary artery disease by cardiokymographic apparatus and to the improved cardiokymographic apparatus for this purpose. It has been known for some years that abnormal displacement of the whole heart, such as recorded by apexcardiography, and of segments of the heart, as recorded by filming the movement of radiopaque chemicals injected into the cardiac chamber (cineangiocardiography), occur in the presence of coronary artery disease in man. However, prior to this invention, there has been no reliable noninvasive technique for screening patients for the presence of coronary artery disease.

In accordance with the method of the present invention, movements of selected segments of the heart are recorded by cardiokymographic means, using a sensor or detector appropriately positioned over the chest of a person being screened, and, simultaneously, higher-frequency movements due to heart valve closures during the cardiac cycle are also detected and recorded using the same apparatus. Then, the resulting recordings of heart movements are analyzed in relation to the timing of the cardiac cycle, as indicated by the detected valve closures, in order to detect any abnormalities of contraction which may be indicative of coronary artery disease.

The displacement cardiograph (DCG) apparatus from which the present invention apparatus was developed has been described in detail in several publications, for example, "The Displacement Cardiograph," by R. Vas et al., IEEE Transactions on Biomedical Engineering, Vol BME-23, No. 1, Jan., 1976, pp. 49–54, and other papers referenced therein. As shown in FIG. 1, the DCG apparatus includes a detector in the form of a detector coil 10, which is positioned on the chest over the heart segment selected for examination, in order to detect movements in the heart segment, which are then reflected in corresponding changes in inductance of the detector coil as the heart segment moves relative to the coil. The detector 10 forms part of a tuned circuit of a self-excited oscillator 12, the frequency of which undergoes changes when the detector coil is positioned at varying distances with respect to external objects.

If the coil 10 is brought near metal, for example, its apparent inductance will decrease, resulting in an increase in the frequency of the variable oscillator circuit 12. However, the presence of a dielectric material near the coil 10 results in an increase in the apparent inductance, and a corresponding decrease in the frequency of the variable oscillator 12.

The output of the variable oscillator circuit 12 is connected by line 14 as an input to a mixer circuit 16, another input of which is derived from a reference oscillator circuit 18, over line 20. The function of the mixer 12 is to subtract one of the two frequencies from the other, and to produce a signal at the difference frequency on output line 22. Typically, the frequency of the reference oscillator 18 is approximately 10 megahertz, with the frequency of the variable oscillator circuit 12 varying about this basic level by a few hundred kilohertz.

The output line 22 from the mixer 16 is connected to a frequency-to-voltage converter 24, which produces an output voltage directly proportional to the input frequency. This voltage is then transmitted over line 26 to a measuring system 28, and recorded by a recorder 30, which may be moving chart recorder or any other convenient recording device.

The effect of dielectric materials on the detector coil 10 is extremely small, and the coil can be utilized to measure the motion of body tissue in its vicinity only when coupled with electronic apparatus of very high sensitivity and low noise characteristics. Additionally, a coil type probe of the type used with the DCG apparatus is ineffective for obtaining useful results with the apparatus and method of the present invention.

The cardiokymograph apparatus of the invention, as shown in FIG. 2, uses as a detector a capacitor plate 32. The plate 32 utilizes an electric, rather than a magnetic, field in the detection of movements of body tissue. The movements cause variations in the capacitance between the plate 32 and ground, and these variations result in corresponding frequency fluctuations in the signal output from the variable oscillator 12. The plate 32 has the advantages of higher sensitivity, improved frequency response, and reduced distortion due to noise.

The plate 32 is more fully illustrated in FIG. 3 of the drawings and is shown as a flat metal disc which is generally circular in shape. However, discs of square or other non-circular cross sections may be used if desired. As an alternate embodiment, the disc 32 may be encapsulated in a plastic or other form of dielectric jacket 34. In this way, the disc can be supported in spaced relationship to the body tissue and, due to the fact that electric field measurements are being obtained, the plastic jacket 34 will not interfere. If desired, a suitable device could be constructed in order to hold the plate 32 in a desired spatial relationship to the body tissue, although this is not necessary in the present invention.

FIG. 5 illustrates another form of detector which may be used in accordance with the present invention, and, in this case, the detector includes a conically shaped metallic element 36 housed within a plastic jacket 38. It has been found that the probe does not necessarily generate a uniform signal across its length due to the fact that a large portion of the signal is generated in a localized area adjacent to the body tissue. Moreover, due to the fact that the mass decreases with the increase in radius of the disc, the signal generated across the disc is not necessarily proportional. The detector of FIG. 5 obviates this problem in that the metal detector section 36 is also of a conical shape, essentially inverse to a plot of the output across the probe. For purposes of convenience, the metal section 36 may be enclosed within the plastic jacket.

By virtue of using detectors of this type, the increased amount of metal provides a much greater degree of sensitivity. Moreover, by virtue of the fact that the apparatus of the present invention operates on the basis of measurement through an electric field, the plate 32 or the other embodiments of the detector can be used. Even more so, it has been found in connection with the present invention that the electric field is much greater than and dominates the electromagnetic field which is generated by movement adjacent to body tissue. In addition, it has been found that the detectors of the type described herein are much easier to use and cost far less to manufacture.

Due to the fact that the plate essentially operates as a capacitor, it would not operate as a type of metal detector which is the case with the DCG apparatus and other apparatus of the prior art. Accordingly, the method and the apparatus of the present invention can be used with equal effectiveness with a patient having artificial components in his body.

In the DCG apparatus of the prior art, some of the frequency shift may have resulted from a change in distributed capacitance. However, with the apparatus of the present invention, the capacitance effect is very substantial and the measurement is based upon at least about 99% of capacitive effect.

With a disc-like probe of the type illustrated in FIGS. 3 and 4, the plate should have a diameter of about no greater than five centimeters and no smaller than about 2.5 centimeters. Plates with a larger size will detect too great a segment of the heart, thereby making it more difficult to determine an abnormality present in normal heart tissue. Detectors smaller than 2.5 centimeters will not have sufficient sensitivity in spite of decreased capacitance but will require high amplification.

In the cardiokymographic apparatus of the present invention, the apparatus employs a variable oscillator 39 which is similar to the oscillator 12 used in the DCG apparatus. However, the output of the oscillator 39 of the present invention is processed by circuitry which utilizes entirely different principles from those used in the DCG apparatus.

As shown in FIG. 2, the circuitry comprises a phase-lock system which includes a signal buffer 40 for receiving signals from the variable oscillator 39, a phase comparator 42, a voltage-controlled oscillator 44, a low-pass filter 46 and an amplifier 48. The variable-frequency signal from the variable oscillator 39 is transmitted to the phase comparator 42 via the buffer 40, and is there compared with a signal from the voltage-controlled oscillator 44.

The phase comparator 42 generates an output signal on line 50 proportional to the phase difference between the input signals from the variable oscillator 12 and the voltage-controlled oscillator 44. This phase-difference signal is filtered in the low-pass filter 46, to eliminate any high-frequency noise, amplified in the amplifier 48, and fed back over line 52 to the voltage-controlled oscillator 44 in such a manner that the frequency of voltage-controlled oscillator will closely follow the varying frequency of the variable oscillator 12. The voltage-controlled oscillator 44 has a fundamental frequency at which it oscillates when no control voltages is applied to it, and will oscillate at a different frequency only when a control voltage is applied over line 52.

It will be apparent that the voltage on line 52 will provide a signal indicative of the displacement of body tissue with respect to the detector plate 32. If there is no body tissue movement with respect to the plate 32, the signal on line 52 will be constant. When the tissue moves to a new position with respect to the plate 32, this will be reflected in a different frequency in the variable oscillator 12, and in a different voltage on line 52. This signal on line 52 is also transmitted to the measuring system and amplifier 28, and thence to the recorder 30. The phase-lock system of the invention has the advantage of being much more sensitive than the frequency-modulation system of the DCG shown in FIG. 1. The phase-lock system is also more economical to construct, and may be obtained, if desired, with much of the circuitry on a single integrated-circuit chip.

In accordance with a very important aspect of the cardiokymograph invention, the signal output from the amplifier 48 is also transmitted over line 56 to a band-pass filter 58, which passes frequencies in the range 30–400 hertz. The signal, passed by the filter 58 include those derived from the audio-frequency movements of the heart, and these are separately measured and recorded by a separate measuring system 60 and recorder 62, which operates simultaneously with the first mentioned recorder 30. The recorders 30 and 62 may, of course, be integrated into a single multiple-input recording device.

The electronic circuits required to perform the functions described herein and illustrated in the block diagram of FIG. 2 are conventional and well known in the electronic art. The oscillators are preferably of the Clapp type, for high stability, the components of the phase-lock system are well known in the art, and the measuring systems 28 and 60 are conventional control units for recorders, typically having an amplifier (not shown) with a centering or zero adjustment and a gain control.

FIG. 6 is a schematic representation of a graph showing the signal which is detected by and processed in the prior art DCG apparatus. As indicated above, this signal provides a recording of tissue segment movement, but without any reference to timing cycles with respect to the tissue. Particularly, this DCG apparatus utilizes a signal from about 0 to 200 hertz which is relatively constant and also requires a separate and independent device for timing of the cardiac cycle, as for example, a device to produce a phonocardiograph. The phonocardiograph, for example, had to be very carefully controlled with respect to the DCG apparatus to ensure that the cardiac time cycle was closely related to cardiac movement as determined by the DCG apparatus.

FIG. 7 more fully illustrates the two frequency spectrum signal components which are descriminated in the apparatus of the present invention. In this case, the low frequency component is shown as being from 0 to 10 hertz with the high frequency component being shown from 30 to 200 hertz.

As indicated above, in the conventional DCG apparatus, the signal which was detected had a frequency response within the range of about 0 to 200 hertz. In the cardiokymographic apparatus of the present invention, the bandpass filter 46 enables the processed signal to be divided into a first signal component of about 0 to about 10 hertz with a second signal component having a band width of about 30 to 200 hertz. The lower frequency signal component in the range of 0 to 10 hertz carries information regarding movement of the body tissue, as for example, movements of cardiac segments. The high frequency signal, that is the signal within the range of 30 to 200 hertz or more, carries information regarding the time frame of the cardiac cycle. In this case, the time frame of the cardiac cycle is based upon the closure and the opening of the heart valve.

It has been found in the present invention that is is not necessary to use a separate device in order to obtain the time frame of the cardiac cycle, as for example, as by a phonocardiograph. Indeed, it has been discovered that the heart wall motion actually contains the phonocardiograph information and this information is sensed in the single signal obtained by the apparatus of the present invention and then separated into the signal components. Moreover, it was not even recognized heretofore that the heart motion actually contained a low frequency signal component representing heart segment movement and a high frequency component which provides information regarding signals representative of sounds. In essence, Applicants have found that by measuring the electric field as a result of heart movement, it is possible to obtain a signal containing a low frequency component providing information regarding heart segment movement and a high frequency signal containing information on valve closures in the heart to represent the cardiac cycle, all in the same frequency spectrum.

The present invention is also unique in that the detector which couples with an electric field is capable of picking up the high frequency signals of very low amplitude, even though these signals could not picked up, even by a high powered microphone.

FIG. 8 represents a plot of a low frequency signal and a high frequency signal which would be depicted on any type of visual rendering device, as for example, the recorders 30 and 62. In this case, it can be observed that one pen of the recorder can record the low frequency signal component, designated as "LFC", and another pen of the recorder would record the high frequency signal components, designated as "HFC". The low frequency signal component illustrates the contraction and relaxation of a particular segment of the heart, while the high frequency signal shows the first valve closure designated as $S_1$, and the second valve closure movement designated as $S_2$. The time segment between these two signals on the high frequency component represents the cardiac cycle and, in this case, the systolic movement in the cardiac cycle, with this systolic movement being designated by reference letter S.

It should also be observed that the cardiokymograph apparatus can also record both the high frequency component and the low frequency component on a single recorded signal or signal output, as for example in FIG. 9 of the drawings. In this case, the first valve closure is designated on the low frequency signal component output recording as $S_1'$ and the second valve closure movement is designated on the high frequency signal component recording as $S_2'$. In either case, it can be observed that the higher frequency component provides a proper time for the cardiac cycle in which to determine the movement of the cardiac segments during the cardiac cycle time frame.

The information provided by the recordings as illustrated in FIGS. 8 and 9 represents a significant advance in the detection of coronary disorders and coronary disease. It has been established that unless the cardiac segment movement was related to the proper cardiac cycle time frame, it is difficult to determine where an abnormal tracing might exist. In essence, this can only be done when the period of cardiac systole has been determined. Heretofore, it was unobvious that a single electric segment existing at the tissue of the body and containing information representative of sound frequencies would provide information relating both to the cardiac cycle as well as to movements of the cardiac segments. By virtue of electric field detection and capacitive measurement therein, it is now possible to obtain readings of very low frequency signals and even very accurate readings of the high frequency signals, even though at low amplitude.

FIG. 10 shows a part of the frequency as a function of the amplitude of the signal in the electric field adjacent to the overlying tissue of the heart. In this case, it can be observed that the amplitude of the signal decreases at about 10 hertz and remains somewhat constant to about 100 hertz. Thereafter, the signal amplitude drops significantly. Thus, it has been observed that it is possible to literally use a single tracing as illustrated in FIG. 9 of the drawings in order to show both the low frequency signal component and the high frequency signal component on a single tracing. Even more so, it is important to note with respect to the present invention that the first signal component can be measured from zero to ten or otherwise from zero to thirty hertz with the second signal component being measured from zero to 100 hertz. This unique result arises from the fact that after 30 hertz frequency, the amplitude is somewhat constant but is decreasing in a relatively low amplitude with respect to the low frequency segment of zero to 10 hertz.

In practicing the method of the invention, the detector plate 32 may be fastened to a suitable stand (not shown) or strapped against the chest of the person being examined. It will be understood, however, that the operation of the cardiokymograph detector 32 does not depend upon contact with the chest wall. On the contrary, the detector plate 32 is normally located so that it is close to, but not in contact with, the person's chest, since it is very important to prevent the transmission of chest vibration produced by the heart beat. For this reason, the detector 32 may include the electrically nonconductive spacer as described above, which will contact the chest and hold the detector itself at a constant spacing therefrom. During the testing period, the person being tested is instructed not to breathe for a few seconds, in order to further reduce the likelihood of recording chest motion. As an alternative, the respiratory artifact could be removed by appropriate processing of the resultant displacement signal.

In order to understand the significance of the cardiokymograph recordings obtained in this manner, it should be recalled that the frequency of oscillation of the variable frequency oscillator circuit 39 is dependent upon the relative proximity of the detector plate 32 to the body tissue of which the movement is being monitored. Thus, as a heart segment moves back and forth with respect to the detector plate 32, the frequency of the variable oscillator circuit 39 moves up and down in synchronism with the movement of the segment. This frequency shift is translated into a varying voltage by the components of the phase-lock system, as already described, and is displayed on the recorder 30. Thus, the cardiokymograph recording represents a plot of the relative position of the heart segment with respect to the plate 32.

In the preferred aspect of using the method of the present invention, the detector is normally placed over the heart in order to determine motions in certain particular areas of the heart. Thus, for example, motions of the anterior wall of the heart lie under certain anatomic points, as for example, $V_2$, $V_3$ and $V_4$. The detector will also be placed over the posterior wall of the heart, as for example, at anatomic points $V_9$ and $V_{10}$. In addition, the detector will also be placed over the lateral wall of the heart, as for example, at anatomic point $V_6$.

In FIG. 11, the movements of a normal heart are shown, by way of background, in the form of a "CKG" tracing 68, which can be seen in relation to the familiar QRS complex 70 of an accompanying electrocardiogram 72, and to the first and second heart sounds, indicated by S1 and S2 on an accompanying phonocardiogram 74. It will be seen that, after the electrical activity of the heart, indicated by the QRS complex 70, there is a small but significant delay before there occurs a corresponding mechanical activity, indicated by an upstroke 75 in the CKG tracing 68. During this upstroke 75, the myocardium (the muscular tissue of the heart wall) is rotating and changing curvature prior to its substantial contraction, indicated by the subsequent downstroke 76 in the CKG tracing. Following contraction is a short period of substantially zero movement, known as the isovolumetric relaxation period, indicated by 77. Then, during the period indicated by 78, the heart ventricle expands rapidly and is subjected to what is usually referred to as the "rapid filling wave." Finally, the phase of the cardiac cycle referred to as diastole is completed during a "slow filling wave" indicated by 79.

The three sets of recordings of FIG. 3 were taken, respectively, at rest, two minutes after exercise and seven minutes after exercise. The recordings taken two minutes after exercise clearly show the development of an abnormal bulge in the CKG tracing, indicated by the arrow 80, positioned in the late systolic phase of the cardiac cycle and corresponding to the contraction period 76 of the normal tracing of FIG. 11. The bulge 80 is indicative of movement of the heart segment in a direction opposite to that in which it normally moves at the time of the cycle, and is a contraction abnormality probably due to the presence of coronary artery disease. As can be seen in the third of the CKG tracings in FIG. 3, and indicated at 82, seven minutes after exercise the bulge has somewhat flattened, and the cardiokymographic recording is gradually reverting to a more normal condition.

The sensitivity and specificity of the method and apparatus of the CKG invention, compared to simultaneously obtained standard electrocardiogram treadmill tests, are shown in Tables I and II. It is apparent from these tables that the invention provides a dramatic improvement over the ECG screening procedure for coronary disease, which is presently the most widely used procedure.

TABLE I

SUMMARY OF TEST RESULTS

| Stress ECG | Stress CKG | Coronary Artery Disease Yes | Coronary Artery Disease No |
|---|---|---|---|
| Abnormal | Abnormal | 25 | 0 |
| Normal | Normal | 2 | 23 |
| Abnormal | Normal | 4 | 6 |
| Normal | Abnormal | 25 | 3 |
| Totals: | | 56 | 32 |

TABLE II

DIAGNOSTIC ACCURACY

| ECG Interpretation | Angiogram Disease | Angiogram Normal | CKG Interpretation | Angiogram Disease | Angiogram Normal |
|---|---|---|---|---|---|
| Abnormal | 29 | 6 | Abnormal | 50 | 3 |
| Normal | 27 | 26 | Normal | 6 | 29 |
| | 56 | 32 | | 56 | 32 |

Diagnostic Accuracy: ECG 63% CKG 90%

As Table I shows, a total of 88 persons were tested, of which 56 were proven to have coronary atherosclerosis and 32 were found to be normal by means of a subsequent coronary angiogram. The table indicates the degree of agreement between the angiogram and the ECG and CKG tests. For example, the ECG test correctly diagnosed the presence of coronary artery disease in 29 of the 56 persons who actually had the disease, and correctly diagnosed the absence of coronary artery disease in 26 of 32 persons who actually did not have disease. The diagnostic accuracy of the ECG was therefore 55/88 or 63%. In contrast, the CKG test correctly diagnosed the presence of coronary heart disease in 50 of the 56 patients with disease, and the absence of disease in 29 of the 32 normal subjects. The diagnostic accuracy of the CKG was, therefore, 79/88, or 90%, significantly better than the ECG.

It will be appreciated that the apparatus of the invention may be used to detect other abnormalities of the heart. In addition to detecting heart vibrations due to valve closure as already described, the apparatus can also detect and record all abnormal heart sounds normally detected by the physician's stethoscope or by audio recording devices. Thus, the CKG device represents the first and only device capable of recording an objective representation of what the physician hears and palpates during his physical examination. This includes, but is not limited to, the so-called third and fourth heart sounds, which are usually indicative of cardiac disease, intracardiac murmurs between the two primary valve closure sounds, which might occur with a variety of diseases of the heart, and which were previously recordable only by the phonocardiogram, and the palpable thrust of the whole heart, which was previously recordable only by the apexcardiogram. Since the ability of the human ear to perceive low-frequency sounds in the 40–60 hertz range is very poor, the CKG is a superior device for such abnormal sounds as the third and fourth heart sounds, which lie in this frequency range.

The apparatus of the invention can also be used in the detection of non-cardiac abnormalities by recording arterial movements at various locations. A loss or diminution of pulsation along an artery, or a substantial difference in such movement between one side of the body and the other, may be indicative of a local vascular obstruction. The CKG device of the invention has been found to be of extraordinary value in detecting differences in pulsation in all organs or locations, regardless of whether or not they are accessable to direct palpation. Such an example is diminished arterial pulsation within the eyeball, which is known to be indicative of the presence of localized vascular disease in the blood vessel leading to the brain.

It will be appreciated, therefore, from the foregoing description that the present invention represents a significant advance in the field of detection and diagnosis of cardiovascular disease in general. In particular, the invention provides a novel method for the detection of coronary artery disease using cardiokymographic apparatus, and novel cardiokymographic apparatus which may be used in the detection of coronary artery disease, as well as in the detection of various other cardiovascular conditions relating to the cardiovascular, cerebrocascular and peripheral vascular systems. Although the invention has been described in relation to a specific embodiment for purposes of illustration, it will be understood that various modifications may be made without departing from the spirit and scope of the invention. Accordingly, the invention is not to be limited, except as by the appended claims.

Having thus described our invention in general terms, what we desire to claim and secure by letters patent is:

1. A method of detecting and diagnosing abnormalities in body tissue utilizing cardiokymographic techniques, said method comprising:

(a) positioning a detector close to the tissue of a person being tested and over a selected segment of said tissue, (b) passing current through said detector to generate an electric field such that the generated electric field will be close to the surface of the person being tested, (c) sensing a change in capacitance in the electric field generated close to the surface of the person being tested as a result of tissue movement and providing a signal at least partially representative of said tissue by the capacitive change in said electric field, (d) processing the signal representative of said tissue movement and separating the signal into a low frequency signal component representative of tissue movement and a high frequency signal component representative of an audible manifestation of the tissue movement, (e) depicting the low frequency signal component to represent the tissue movement and depicting the high frequency signal component to providing timing with respect to the tissue movement, and (f) and analyzing said depicted portion of said signal components to determine any abnormality in the tissue movement.

2. The method of claim 1 further characterized in that the step of processing the signal comprises filtering the signal representative of tissue movement to obtain the first signal component providing information about the tissue movement, and the second signal component providing information about the time frame of said tissue movement, said method also comprising correlating the information of said tissue movement to said time frame in order to determine if an abnormality was present in response to the tissue movement.

3. The method of claim 1 further characterized in that said method is used in the diagnosis of coronary abnormality, said step of positioning comprises the positioning of said detector close to the chest of a person being tested and over a selected segment of the heart.

4. The method of claim 3 further characterized in that the high frequency signal component is depicted simultaneously with the low frequency signal component.

5. The method of claim 4 further characterized in that an ECG is taken simultaneously of the person in whom tissue movement is being measured and is simultaneously depicted with the low frequency signal component and high frequency signal component.

6. A method utilizing cardiokymographic apparatus in the detection and diagnosis of coronary atherosclerosis, said method comprising the steps of:

(a) positioning a cardiokymograph detector close to the chest of a person being tested, over a selected segment of the heart, or over a selected portion of the arterial system of a person, (b) detecting and depicting movement of the heart segment or an artery of the person when at rest, using cardiokymographic apparatus, (c) detecting and depicting movement of the same heart segment or the same artery during a stress condition such as after strenous exercise, again using the cardiokymographic apparatus, (d) simultaneously with each of said detecting steps, detecting audio frequency events with respect to said heart segment or said same artery which have a timed physiological relationship to the movement thereof, and depicting such events indicative of the timing of the cardiac cycle using the cardiokymographic apparatus itself, (e) analyzing the cardiokymographic depictions of movement so produced, in relation to the audio frequency events representative of the timing of the cardiac cycle, to determine the presence and degree of any contraction abnormality of the heart segment, or the artery and (f) determining from the analysis of the cariokymographic depictions whether or not the person has coronary atherosclerosis.

7. A method as set forth in claim 6, wherein said step of detecting and depicting events indicative of the timing of the cardiac cycle includes detecting movement induced by closure of the heart valves using the cardiokymographic apparatus itself.

8. A method as set forth in claim 7, wherein said step of detecting movement induced by closure of the heart valves includes:

filtering signals in the cardiokymographic apparatus to exclude components derived from relatively slow movements of the heart segment or segments caused directly by cardiac contraction and relaxation, and amplifying the remaining signal components to provide an indication of valve closure sounds.

9. A method as set forth in claim 7, wherein said step of depicting comprises the recording of the events on a recording device.

10. A method as set forth in claim 6, wherein said step of detecting and recording events indicative of the timing of the cardiac cycle includes detecting movement of an artery using the cardiokymographic apparatus itself.

11. An apparatus for measuring movement of body tissue and determining abnormality or disease therefrom, said apparatus comprising:

(a) a variable-frequency oscillator circuit, (b) detector means in which the electrical impedance depends upon the proximity of the detector means with respect to body tissue, said detector means being coupled to said variable-frequency oscillator circuit for determining, at least in part, its frequency of oscillation, (c) means associated with said detector means for causing generation of an electric field with said body tissue and adjacent said body tissue, said detector means detecting a change in the capacitance in the electric field adjacent the body tissue, (d) voltage controlled oscillator means for providing a reference signal, (e) phase-lock-loop circuit means coupled to said variable-frequency oscillator circuit, said phase-lock-loop circuit means comprising phase comparison means for generating an error signal indicative of a phase difference between a signal received from said variable frequency oscillator circuit and said reference signal to thereby produce a signal indicative of the displacement of body tissue, and which is at least based on the detected capacitive changes with respect to said detector means, and (f) measuring and depicting means to depict said signal indicative of the displacement.

12. An apparatus as set forth in claim 11, wherein:

said phase-lock-loop circuit means includes an amplifier, said voltage controlled oscillator means in a voltage controlled oscillator and said phase comparison means is a phase comparator, said phase comparator is connected to generate an error signal indicative of a phase difference between the signals from said variable-frequency oscillator circuit and from said voltage-controlled oscillator, and said amplifier is connected to amplify said error signal and transmit it as a control voltage to said voltage-controlled oscillator, and said amplified error signal is coupled to said measuring and depicting means to provide a measure of displacement of body tissue with respect to said detector means.

13. An apparatus as set forth in claim 1, wherein said depicting means is a recording means.

14. Cardiokymographic apparatus as set forth in claim 11, wherein said detector means includes a capacitor plate permitting an associated electric field to be established between said plate and a segment of body tissues and which plate exists with respect to a reference potential, and which capacitance will vary according to the position of the plate relative to a segment of body tissue under examination.

15. Cardiokymographic apparatus as set forth in claim 12, and further including:

filter means for isolating components of signals derived from said phase-lock-loop circuit means, which components are substantially in the audio-frequency range, amplifying means to amplify the isolated audiofrequency signal components, and recording means for recording the amplified signal components.

16. The cardiokymographic apparatus as set forth in claim 9 further characterized in that said detector means comprises a generally flat metal plate.

17. The cardiokymographic apparatus as set forth in claim 9 further characterized in that said detector means comprises a generally flat metal plate and a dielectric jacket disposed around said plate so that the jacket can be placed on the body of the person being tested and with the plate being spaced from the body.

18. The cardiokymographic apparatus as set forth in claim 11 further characterized in that said detector means comprises a metal member having a configuration such that the member has a high center portion relative to the external surface with portions of the member being constantly spaced downwardly from said high center portion in proportion to the distance outwardly from said high center portion.

19. The apparatus of claim 11 further characterized in that means is coupled to receive the signal from the phase-lock-loop circuit means for separating the signal into a low frequency component representative of the tissue movement and a high frequency signal component representative of an audible manifestation of the tissue movement, and the measuring and depicting means depicts the low frequency signal component to represent the tissue movement and depicts the high frequency signal component to provide timing with respect to the tissue movement.

20. The apparatus of claim 19 further characterized in that measuring and depicting means is provided with means to depict the high frequency signal component simultaneously with the low frequency signal component.

21. The apparatus of claim 20 further characterized in that an ECG is taken simultaneously of the person in whom tissue movement is being measured and is simultaneously depicted with the low frequency signal component and high frequency signal component.

22. Apparatus for detecting and diagnosing abnormalities in body tissue utilizing cardiokymographic techniques, said apparatus comprising:

(a) a detector for positioning close to the tissue of a person being tested and over a selected segment of said tissue, (b) means coupled to said detector for passing current through said detector to generate an electric field such that the generated electric field will be close to the surface of the person being tested, (c) means for sensing the electric field generated close to the surface of the person being tested as a result of tissue movement and providing a signal representative of a change in the capacitance of the electric field as a result of said tissue movement, (d) means for separating the signal into a low frequency signal component representative of tissue movement and a high frequency signal component representative of an audible manifestation of the tissue movement, and (e) means operatively connected to the means for separating for depicting the low frequency signal component to represent the tissue movement and depicting the high frequency signal component to provide timing with respect to the tissue movement in order to analyze and depicted portions of the signal to determine any abnormality in the tissue movement.

23. The apparatus of claim 22 further characterized in that said apparatus comprises means for filtering the signal representative of tissue movement to obtain a first signal component providing information about the tissue movement, and a second signal component providing information about the time frame of said tissue movement so that the information of said tissue movement can be correlated to said time frame.

24. The cardiokymographic apparatus of claim 22 wherein said depicting means is a recording means.

25. The apparatus of claim 22 further characterized in that said apparatus is used in the diagnosis of coronary abnormality, and with said detector being designed to be positioned close to the chest of a person being tested an over a selected segment of the heart.

26. The apparatus of claim 25 further characterized in that means is provided with the means for depicting to depict the high frequency signal component simultaneously with the low frequency signal component.

27. The apparatus of claim 26 further characterized in that an ECG is taken simultaneously of the person in whom tissue movement is being measured and is simultaneously depicted with the low frequency signal component and high frequency signal component.

28. Cardiokymographic apparatus having a variable oscillator circuit, a detector element connected to said variable oscillator circuit so as to determine, at least in part, the frequency of said variable oscillator circuit; circuit means coupled to said variable oscillator circuit to provide an output signal indicative of the frequency of said variable oscillator circuit and hence indicative of the position and movement of body tissue with respect to said detector element, and measuring and recording means, wherein the improvement comprises:

said circuit means comprises a voltage controlled oscillator means for providing a reference signal, said circuit means also comprises a phase-lock-loop having a phase comparison means for generating an error signal indicative of a phase difference between a signal indicative of the frequency of the variable oscillator circuit and said reference signal, filter means for separating signals output from said circuit means which are in the audio-frequency range, from those of relatively low frequency which are indicative of heart segment movements;

amplifying means for amplifying the audio-frequency signals passed by said filter means; and said measuring and recording means recording the amplified audio-frequency signals simultaneously with recording of the low frequency signals indicative of heart segment movements for comparison of the audio-frequency signals with recordings of the unfiltered signal indicative of heart segment movements to thereby provide a timing of the heart segment movements.

29. Cardiokymographic apparatus as set forth in claim 28, wherein said filter means inhibits the passage of signals having frequencies below approximately 30 hertz.

30. Cardiokymographic apparatus as set forth in claim 28, wherein said detector element includes a capacitor plate permitting an associated electric field to exist with respect to a reference potential, and which capacitance will vary according to the position of the plate relative to a segment of body tissue under examination.

31. The apparatus of claim 28 further characterized in that the improvement comprises means for taking an ECG simultaneously of the person in whom tissue movement is being measured and for simultaneously depicting the ECG with the low frequency signal component and high frequency signal component.

32. The apparatus of claim 31 further characterized in that said improvement comprises means for passing current through an electric field such that the generated electric field will be close to the surface of the person being tested.

33. The apparatus of claim 32 wherein the improvement comprises: a capacitor plate in said detector element, having an associated electric field and a capacitance with respect to a reference potential, and which capacitance will vary according to the relative position of the plate with respect to a segment of body tissue under examination.

*34. A method of detecting and diagnosing abnormalities in body tissue utilizing cardiokymographic techniques, said method comprising:*

*(a) positioning a detector close to the tissue of a person being tested and over a selected segment of said tissue,*

*(b) passing current through said detector to generate an electric field such that the generated electric field will be close to and may extend to the surface of the person being tested,*

*(c) sensing a change in capacitance of the detector which results from tissue movement, and providing a low frequency signal at least partially representative of said tissue movement,*

*(d) processing the signal representative of said tissue movement and depicting a portion of said signal to represent tissue movement,*

*(e) generating a signal representative of the timing of a cycle of the tissue which is moving and which is independent of the signal representative of the tissue movement,*

*(f) depicting the signal representative of timing to thereby provide timing with respect to the tissue movement, and*

*(g) analyzing said depicted portion of said signals to determine any abnormality in the tissue movement.*

*35. The method of claim 34 further characterized in that said method comprises generating a signal representation of the timing using the same transducer used to generate the signal representative of tissue movement.*

*36. The method of claim 34 further characterized in that said method comprises generating a signal representative of the timing from an apparatus independent of the detector.*

*37. The method of claim 34 further characterized in that said method comprises processing the signal providing information about the timing of the cycle of said tissue movement, said method also comprising correlating the information of said tissue movement to the timing of the cycle in order to determine if an abnormality was present in response to the tissue movement.*

*38. The method of claim 34 further characterized in that said method is used in the diagnosis of coronary abnormality, said step of positioning comprises the positioning of said detector close to the chest of a person being tested and over a selected segment of the heart.*

*39. The method of claim 34 further characterized in that the body tissue is the heart or a portion of an arterial system of a person and said cycle is the systolic interval of the heart.*

*40. The method of claim 39 further characterized in that said method comprises generating a tracing using cardiokymographic techniques and a bulge in said tracing is indicative of a contraction abnormality which is predictive of coronary artery disease.*

*41. The method of claim 34 further characterized in that said method comprises filtering a signal resulting from a change in capacitance of the detector to separate and extract the low frequency signal therefrom.*

*42. The method of claim 41 further characterized in that the frequency components of said low frequency signal are primarily in the range of about 0 to about 30 hertz.*

*43. The method of claim 41 further characterized in that the frequency components of said low frequency signal are primarily in the range of about 0 to about 10 hertz.*

*44. A method utilizing cardiokymographic apparatus in the detection and diagnosis of coronary atherosclerosis, said method comprising the steps of:*

*(a) positioning a detector close to the chest of a person being diagnosed, when at rest, over a selected segment of the heart or over a selected portion of the arterial system of a person,*

*(b) sensing a change in capacitance of the detector which results from tissue movement of the person being diagnosed during rest,*

*(c) generating a signal representative of the change in capacitance,*

*(d) processing the signal representative of the change in capacitance in order to determine movement of the heart segment or arterial system of the person during rest,*

*(e) depicting movement of the heart segment or an artery in the arterial system of the person when at rest,*

*(f) positioning a detector close to the chest of a person being diagnosed, during a stress condition, such as after or during exercise, and over the selected segment of the heart or over the selected portion of the arterial system of the person,*

*(g) sensing a change in capacitance in the electrical field generated close to the surface of the person being diagnosed during a stress condition such as after or during exercise, and which change also results from at least tissue movement,*

*(h) generating a signal representative of the change in capacitance from the person being diagnosed during or after exercise,*

*(i) processing the signal representative of the change in capacitance of the person during or after exercise to determine movement of the heart segment or arterial system of the person during or after exercise,*

*(j) depicting movement of the same heart segment or the same artery during such stress condition,*

*(k) simultaneously with each of said sensing and depicting steps, detecting other events with respect to said heart segment or said same artery which have a timed physiological relationship to the movement thereof, and depicting such events indicative of the timing of the cardiac cycle,*

*(l) analyzing the depictions of movement so produced, in relation to the other events representative of the timing of the cardiac cycle, to determine the presence and degree of any contraction abnormality of the heart segment or the artery, and*

*(m) determining from the analysis of the depictions whether or not the person has coronary atherosclerosis.*

*45. The method of claim 44 further characterized in that said method comprises detecting such other events with the cardiokymograph apparatus.*

*46. The method of claim 44 further characterized in that said method comprises detecting such other events with an apparatus independent of the cardiokymograph apparatus.*

*47. The method of claim 44 further characterized in that said method comprises detecting such other events with an electrocardiograph apparatus.*

*48. The method of claim 44 further characterized in that said method comprises detecting such other events which are audio frequency events with a phonocardiograph.*

*49. A method as set forth in claim 48 further characterized in that said step of detecting and depicting such other events indicative of the timing of the cardiac cycle includes detecting movement induced by closure of the heart valve.*

*50. A method as set forth in claim 46 further characterized in that said step of detecting such other events includes:*

*filtering signals in the cardiokymographic apparatus to exclude components derived from relatively slow movements of the heart segment or segments caused directly by cardiac contraction and relaxation, and*

*amplifying the remaining signal components to provide an indication of valve closure sounds.*

*51. A method as set forth in claim 50 wherein said step of depicting such other events comprises the recording of the events on a recording device.*

*52. The method of claim 44 further characterized in that the detector is a cardiokymograph detector, and the steps of depicting movement of the heart segment or artery occurs using a cardiokymographic apparatus.*

*53. The method of claim 52 further characterized in that a bulge in a tracing using cardiokymographic techniques is indicative of a contraction abnormality which is predictive of coronary artery disease.*

*54. An apparatus for measuring movement of body tissue and determining abnormality or disease therefrom, said apparatus comprising:*

*(a) an oscillator circuit,*

*(b) detector means in which the electrical capacitance depends at least in part upon the position of the body tissue with respect to the detector means, said detector means being coupled to said oscillator circuit for determining at least in part, its frequency of oscillation,*

*(c) means associated with said detector means for causing generation of an electric field at least adjacent to said body tissue, said detector means detecting a change in the capacitance as a result of body tissue movement,*

*(d) oscillator means in said oscillator circuit for providing a reference signal,*

*(e) reference circuit means coupled to said oscillator means, said reference circuit means comprising a generator for generating a signal indicative of a difference in frequency between a signal received from said oscillator circuit and said reference signal,*

*(f) filter means operatively connected to said reference circuit means to receive the signal indicative of difference and filter therefrom a signal of interest to thereby provide a signal indicative of the displacement of body tissue, and which is at least based on the detected capacitive changes with respect to said detector means, and*

*(g) measuring and depicting means to depict said signal indicative of the displacement.*

*55. An apparatus as set forth in claim 54 wherein said depicting means is a recording means.*

*56. The cardiokymographic apparatus as set forth in claim 54 wherein said detector means includes a capacitor plate permitting an associated electric field to be established between said plate and a segment of body tissue and which plate exists with respect to a reference potential, and which capacitance will vary according to the position of the plate relative to a segment of body tissue under examination.*

*57. The cardiokymographic apparatus as set forth in claim 54 further characterized in that said detector means comprises a generally flat metal plate.*

*58. The cardiokymographic apparatus as set forth in claim 54 further characterized in that said detector means comprises a generally flat metal plate and a dielectric jacket disposed around said plate so that the jacket can be placed on the body of the person being tested and with the plate being spaced from the body.*

*59. The cardiokymographic apparatus as set forth in claim 54 further characterized in that said detector means comprises a generally flat metal plate which is adapted to be supported in spaced relation to exterior body tissue and means is provided to support said plate.*

*60. The cardiokymographic apparatus as set forth in claim 54 further characterized in that said detector means comprises a metal member having an inverse conical shape.*

*61. The cardiokymographic apparatus as set forth in claim 54 further characterized in that said signal of interest is a low frequency signal having a frequency in the range of about 0 to about 30 hertz.*

*62. The cardiokymographic apparatus as set forth in claim 54 further characterized in that said signal of interest is a low frequency signal having a frequency in the range of about 0 to about 10 hertz.*

*63. Apparatus for detecting and diagnosing abnormalities in body tissue utilizing cardiokymographic techniques, said apparatus comprising:*

*(a) a detector for positioning close to the tissue of a person being tested and over a selected segment of said tissue,*

*(b) means coupled to said detector for passing current through said detector to generate an electric field such that the generated electric field will be close to and may extend to the surface of the person being tested,*

*(c) means for sensing a change in the capacitance of the detector which results from tissue movement and providing a signal representative of a change in the capacitance to thereby represent the tissue movement,*

*(d) means for processing the signal representative of said tissue movement,*

*(e) depicting means operatively connected to the means for processing for depicting a portion of said processed signal to represent tissue movement in order to analyze the depicted portion of said signal to determine any abnormality in the tissue movement,*

*(f) means for generating a signal representative of the timing of a cycle of the issue which is moving and which is independent of the signal representative of tissue movement, and*

*(g) means operatively connected to the means for processing to provide timing with respect to the tissue movement in order to analyze said depicted portions of the signal to determine any abnormality in the tissue movement.*

*64. The apparatus as set forth in claim 63 wherein said detector includes a capacitor plate permitting an associated electric field to exist, and where the capacitance will vary according to the position of the tissue under examination with respect to the position of the plate.*

*65. The apparatus of claim 63 wherein said depicting means is a recording means.*

*66. The apparatus of claim 64 further characterized in that said apparatus comprises a filter means for filtering a signal generated by the change in capacitance to extract a low frequency signal and which low frequency signal is the signal representative of the tissue movement.*

*67. The apparatus of claim 66 further characterized in that said low frequency signal has a frequency in the range of about 0 to about 30 hertz.*

*68. The apparatus of claim 66 further characterized in that said low frequency signal has a frequency in the range of about 0 to about 10 hertz.*

*69. A method utilizing cardiokymographic apparatus in the detection and diagnosis of coronary atherosclerosis, said method comprising the steps of:*

*(a) positioning a cardiokymograph detector close to the chest of a person being tested, over a selected segment of the heart, or over a selected portion of the arterial system of a person,*

*(b) sensing a change in capacitance of the detector while the person being tested is at rest and generating a signal representative of movement of the heart or an artery,*

*(c) detecting and depicting movement of the heart segment or an artery of the person when at rest based on such signal, using cardiokymographic apparatus,*

*(d) detecting and depicting movement of the same heart segment or the same artery during a stress condition, such as after or during strenuous exercise, again using the cardiokymographic apparatus,*

*(e) simultaneously with each of said detecting steps, detecting events with respect to said heart segment or said same artery which have a timed physiological relationship to the movement thereof, and depicting such events indicative of the timing of the cardiac cycle,*

*(f) analyzing the depictions of movement so produced, in relation to the events representative of the timing of the cardiac cycle, to determine the presence and degree of any contraction abnormality of the heart segment, or the artery, and*

*(g) determining from the analysis of the cardiokymographic depictions whether or not the person has coronary atherosclerosis.*

*70. A method as set forth in claim 69 wherein said step of detecting and depicting events indicative of the timing of the cardiac cycle includes detecting movement induced by closure of the heart valve.*

*71. A method as set forth in claim 70 wherein said step of detecting movement induced by closure of the heart valve includes:*

*filtering signals in the cardiokymographic apparatus to exclude components derived from relatively slow movements of the heart segment or segments caused directly by cardiac contraction and relaxation, and*

*amplifying the remaining signal components to provide an indication of valve closure sounds.*

*72. A method as set forth in claim 69 wherein said step of depicting comprises the recording of the events on a recording device.*

*73. A method as set forth in claim 69 wherein said step of detecting and recording events indicative of the timing of the cardiac cycle includes detecting movement of an artery.*

*74. The method as set forth in claim 69 further characterized in that said method comprises generating a tracing using the cardiokymographic apparatus and a bulge in said tracing is indicative of a contraction abnormality which is predictive of coronary artery disease.*

*75. A method utilizing cardiokymographic apparatus in the detection and diagnosis of coronary and coronary artery disease, said method comprising the steps of:*

*(a) positioning a cardiokymograph detector close to the chest of a person being tested, over a selected segment of the heart, or over a selected portion of the arterial system of a person,*

*(b) detecting and depicting movement of the heart segment or an artery of the person when at rest during the systolic interval of the heart, using cardiokymographic apparatus,*

*(c) simultaneously with the detecting and depicting steps, detecting other events with respect to the heart segment or said same artery which have a timed physiological relationship to the movement thereof indicative of the systolic interval of a cardiac cycle,*

*(d) depicting such events indicative of the cardiac cycle,*

*(e) detecting and depicting movement of the same heart segment or the same artery during a stress condition, such as after or during strenuous exercise, again using the cardiokymographic apparatus, and where a bulge may be present in a depiction of the movement depending upon the presence of an aflicited portion,*

*(f) simultaneously with said detecting steps during a stress condition, detecting events with respect to said heart segment or said same artery which have a timed physiological relationship to the movement thereof indicative of the systolic interval of a cardiac cycle, during a stress condition, and depicting such events indicative of the timing of the cardiac cycle,*

*(g) analyzing the depictions of movement so produced, in relation to the events representative of the timing of the cardiac cycle to determine possible existence in such depictions of a bulge in an aflicted portion of the heart segment or same artery during normal inward contractions of the remaining portions of said same heart segment or same artery and which is indicative of coronary or coronary artery disease, and*

*(h) determining from the analysis of the depictions whether or not the person has coronary or coronary artery disease.*

*76. A method utilizing cardiokymographic apparatus in the detection and diagnosis of coronary and coronary artery disease, said method comprising the steps of:*

*(a) positioning a cardiokymograph detector close to the chest of a person being tested, over a selected segment of the heart, or over a selected portion of the arterial system of a person and generating a signal representative of movement,*

*(b) processing the signal representative of movement of the heart segment or an artery of the person to remove respiratory artifact,*

*(c) detecting and depicting movement of the same heart segment or the same artery of the person when at rest, using cardiokymographic apparatus,*

*(d) detecting and depicting movement of the same heart segment or the same artery during a stress condition such as after or during strenuous exercise, again using the cardiokymographic apparatus and generating a signal representative of such movement,*

*(e) processing the signal representative of movement of the same heart segment or same artery generated during the stress condition to remove respiratory artifact,*

*(f) simultaneously with each of said detecting steps, detecting events with respect to said heart segment or said same artery which have a timed physiological relationship to the movement thereof, and depicting such events indicative of the timing of the cardiac cycle,*

*(g) analyzing the depictions of movement so produced, in relation to the events representative of the timing of the cardiac cycle, to determine the presence and degree of any contraction abnormality of the heart segment, or the artery, and*

*(h) determining from the analysis of the cardiokymographic depictions whether or not the person has coronary or coronary artery disease.*

*77. The method of claim 76 further characterized in that said method comprises generating a signal representative of the timing using the same transducer used to generate the signal representative of tissue movement.*

*78. The method of claim 76 further characterized in that said method comprises generating a signal representative of the timing from an apparatus independent of the detector.*

*79. The method of claim 76 further characterized in that the method comprises generating such signals as a result of a change in capacitance in an electric field generated close to the chest of a person being tested.*

*80. The method of claim 79 further characterized in that said method comprises filtering a signal resulting from a change in capacitance in the electric field and extracting the low frequency signal therefrom.*

*81. The method of claim 80 further characterized in that said low frequency signal has a frequency in the range of about 0 to about 30 hertz.*

*82. The method of claim 80 further characterized in that said low frequency signal has a frequency in the range of about 0 to about 10 hertz.*

* * * * *